(12) United States Patent
Phan et al.

(10) Patent No.: US 7,208,481 B2
(45) Date of Patent: Apr. 24, 2007

(54) AMINODIPHOSPHONATE APOLIPOPROTEIN E MODULATORS

(75) Inventors: Hieu Trung Phan, Tannay (CH); Lân Mong Nguyen, Nyon (CH); Raymond Azoulay, Genève (CH); Vinh Van Diep, Vétraz-Monthoux (FR); Eric Joseph Niesor, Nyon (CH); Craig Leigh Bentzen, Bogis-Bossey (CH); Yves Gyon Gellin, Ville-la Grand (FR); Anne Perez, Versoix (CH); Jean-Luc Thulliard, Saint Cergue (CH)

(73) Assignee: ILEX Products, Inc., San Antonio, TX (US)

( * ) Notice: Subject to any disclaimer, the term of this patent is extended or adjusted under 35 U.S.C. 154(b) by 0 days.

(21) Appl. No.: 10/504,744

(22) PCT Filed: Feb. 14, 2003

(86) PCT No.: PCT/US03/04358

§ 371 (c)(1),
(2), (4) Date: Nov. 29, 2004

(87) PCT Pub. No.: WO03/070169

PCT Pub. Date: Aug. 28, 2003

(65) Prior Publication Data

US 2005/0075317 A1    Apr. 7, 2005

Related U.S. Application Data

(60) Provisional application No. 60/358,118, filed on Feb. 19, 2002.

(51) Int. Cl.
| | |
|---|---|
| *A61K 31/675* | (2006.01) |
| *A01N 57/00* | (2006.01) |
| *C12Q 1/70* | (2006.01) |
| *C12Q 1/48* | (2006.01) |
| *C12N 9/12* | (2006.01) |

(52) U.S. Cl. .............. 514/89; 514/86; 514/91; 514/92; 514/94; 514/99; 435/4; 435/15; 435/194; 435/325; 435/366

(58) Field of Classification Search ............... 514/107, 514/651, 460, 102, 423, 80, 91; 435/325
See application file for complete search history.

(56) References Cited

U.S. PATENT DOCUMENTS

| | | | |
|---|---|---|---|
| 3,846,420 A | 11/1974 | Wollmann et al. | |
| 3,957,160 A | 5/1976 | Plöger et al. | |
| 4,157,364 A | 6/1979 | Buckman et al. | |
| 4,447,256 A | 5/1984 | Suzuki et al. | |
| 5,393,748 A | 2/1995 | Pohjala et al. | |
| 5,624,917 A * | 4/1997 | Kitano et al. | 514/76 |
| 5,856,314 A | 1/1999 | Kaas et al. | |
| 5,866,556 A | 2/1999 | Heikkilä-Hoikka et al. | |
| 6,057,306 A | 5/2000 | Wilson et al. | |
| 6,303,784 B1 * | 10/2001 | Nguyen et al. | 546/24 |
| 6,416,964 B2 * | 7/2002 | Reszka et al. | 435/15 |
| 2001/0036936 A1 | 11/2001 | Day et al. | |

FOREIGN PATENT DOCUMENTS

WO    WO 99/38998    8/1999

OTHER PUBLICATIONS

Srivastava et al., Estrogen up-regulates apolipoprotein E (ApoE) gene expression by increasing apoE mRNA in the translating pool via the estrogen receptor alpha-mediated pathway' J. Biol. Chem., 272:33360-33366, 1997.*
Lininger-Muller et al., The rat a useful model for pharmacological studies on apolipoprotein E, Life Sciences,58:455-467 (1996).*
Krupinsky (stroke 1997; 28:564-573).*

* cited by examiner

*Primary Examiner*—Ardin H. Marschel
*Assistant Examiner*—Shirley V. Gembeh
(74) *Attorney, Agent, or Firm*—McDonnell Boehnen Hulbert & Berghoff LLP

(57) ABSTRACT

The present invention relates to methods of use of aminodiphosphonate to modulate apolipoprotein E levels and the use of such compounds in therapy, including cardiovascular and neurological disease states.

39 Claims, No Drawings

AMINODIPHOSPHONATE APOLIPOPROTEIN E MODULATORS

FIELD OF INVENTION

The present invention relates to aminodiphosphonate compounds, the processes for their preparation, pharmaceutical compositions containing them and their use in therapy, in particular for modulating (increasing and decreasing) apolipoprotein E in plasma and in tissues.

BACKGROUND OF THE INVENTION

Apolipoprotein E (apoE) is a polymorphic, multifunctional protein synthesized by several cell types and tissues, including liver, kidney, skin, adipose tissue, macrophages and brain. The wide distribution of apoE is associated with the maintenance of key cellular functions such as intracellular cholesterol trafficking, cholesterol distribution between cells, and tissue reparation.

The amino acid sequence of the apoE protein is well conserved throughout species. ApoE can be viewed as a regulator of cholesterol homeostasis in tissues such as the central nervous system (CNS) and peripheral nervous system (PNS) and the arterial wall (cell-cell) or between tissues via the circulating plasma lipoproteins (tissue-tissue).

The major role of plasma apoE containing lipoproteins is to transfer lipids (cholesterol) from peripheral tissues to the liver and to remove excess cholesterol from peripheral tissues via the reverse cholesterol transport system. Dysregulation of this mechanism leads to excess cholesterol deposition in peripheral tissues such as arteries (arteriosclerosis) and skin (xanthomas and xanthelasmas). ApoE has also been shown to have a direct effect on lymphocyte proliferation and thus has an immunomodulatory role.

ApoE is the only lipoprotein synthesized in the brain and has a key role in cholesterol transport between cells of the CNS. Local secretion of apoE by cells such as macrophages or macrophage-derived cells is essential for the uptake of excess tissue cholesterol and the provision of cholesterol for specific needs such as nerve repair and remyelinisation.

Up to the present time, compounds affecting apoE production in vitro and in vivo have not been extensively investigated. Only hormone-like estrogens and corticoids have been shown to change apoE levels under various experimental conditions (Srivastava et al., 1997; Stone et al., 1997).

There is currently a need for compounds that modulate apoE synthesis and secretion, such compounds having application in the treatment of diseases such as atherosclerosis, excess lipid deposition in peripheral tissues such as skin (xanthomas), stroke, memory loss, optic nerve and retinal pathologies (i.e., macular degeneration, retinitis pigmentosa), repair of traumatic damage of the central nervous system (brain tissue), repair of traumatic damage of the peripheral nervous system (i.e., nerve section compression or crush), prevention of the degenerative process due to aging (i.e., Alzheimer's disease), prevention of degenerative neuropathies occurring in diseases such as diabetic neuropathies and multiple sclerosis, autoimmune diseases and activation of the innate immune system.

SUMMARY OF THE INVENTION

As shown herein, certain aminodiphosphonates modulate (increase or decrease) the production of apoE in vitro and in vivo. Thus, one aspect of the present invention is a method of modulating the production of apoE by an apoE producing cell comprising contacting said apoE producing cell with an effective amount of a compound of formula (I):

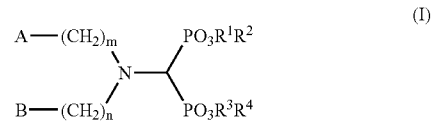

wherein A is an aryl group optionally substituted by one or more substituents independently selected from the group consisting of hydrogen, $C_1$–$C_8$ alkyl, $C_1$–$C_8$ alkoxy, halogen, nitro, amino, and $NR^5R^6$ where $R^5$ and $R^6$ are independently hydrogen or $C_1$–$C_4$ alkyl;

B is hydrogen, $C_1$–$C_8$ alkyl group, or phenyl optionally substituted with one or more substituents independently selected from the group consisting of hydrogen, $C_1$–$C_8$ alkyl, $C_1$–$C_8$ alkoxy, hydroxy, halogen and cyano;

m and n are independently selected are an integer from zero to 10, $R^1$, $R^2$, $R^3$ and $R^4$ are independently hydrogen or $C_1$–$C_6$ alkyl, or a pharmaceutically acceptable salt thereof.

In various embodiments, A is an optionally substituted pyridyl, pyrazinyl, quinolinyl or benzothiazolyl. In preferred embodiments, A is 2-pyridyl, 3-pyridyl or 3-(2,6-dimethylpyridyl). In some preferred embodiments, B is hydrogen and n is an integer from 0 to 6. In other embodiments, B is an optionally substituted phenyl group which may be phenyl, p-methoxyphenyl or 4-hydroxy-3-methoxy-5-methylphenyl. In some preferred embodiments, $R^1$, $R^2$, $R^3$ and $R^4$ are the same and are methyl, ethyl or isopropyl.

The method provides that the modulation of cellular apoE production comprises increasing or decreasing the production of apoE. In some embodiments wherein the apoE production is increased, the compound of formula (I) is selected from the group consisting of:

tetramethyl N-(2-pyridyl)aminomethylenediphosphonate;
tetraethyl N-(2-pyridyl)aminomethylenediphosphonate;
tetraethyl N-(3-pyridyl)aminomethylenediphosphonate;
tetraethyl N-[3-(2,6-dimethylpyridyl)]aminomethylenediphosphonate;
tetraethyl N-(3-quinolinyl)aminomethylenediphosphonate;
tetraethyl N-[2-(2-pyridyl)ethyl]-N-methyl-aminomethylenediphosphonate;
tetraethyl N-(2-pyridyl)-N-(benzyl)-aminomethylenediphosphonate;
tetraethyl N-(2-pyridyl)-N-(p-methoxybenzyl)-aminomethylenediphosphonate;
tetraethyl N-(2-pyridyl)-N-(n-pentyl)-aminomethylenediphosphonate; and
tetraethyl N-(2-pyridyl)-N-(4-hydroxy-3-methoxy-5-methylbenzyl)-aminomethylenediphosphonate.

In some embodiments wherein the modulation of apoE production is decreased, the compound of formula (I) is selected from the group consisting of:

tetraisopropyl N-(2-pyridyl)aminomethylenediphosphonate;
tetraethyl N-(3-pyridylmethyl)aminomethylenediphosphonate;

tetraethyl N-(2-pyrazinyl)aminomethylenediphosphonate;
tetraethyl N-(2-benzothiazolyl)aminomethylenediphosphonate;
tetraethyl N-(2-pyridyl)-N-methyl-aminomethylenediphosphonate; and
tetraethyl N-(2-pyridylmethyl)aminomethylenediphosphonate.

Another aspect of the present invention provides for a method of modulating apoE levels in a patient in need of such treatment, comprising administration of an effective amount of a compound of formula (I) as described above. Modulation of apoE levels includes modulation of plasma and/or tissue apoE levels. The method provides that the modulation of the apoE levels comprises increasing or decreasing such levels. In some embodiments wherein the apoE levels production are increased, the compound of formula (I) is selected from the group consisting of:
tetramethyl N-(2-pyridyl)aminomethylenediphosphonate;
tetraethyl N-(2-pyridyl)aminometliylenediphosphonate;
tetraethyl N-(3-pyridyl)aminomethylenediphosphonate;
tetraethyl N-[3-(2,6-dimethylpyridyl)]aminomethylenediphosphonate;
tetraethyl N-(3-quinolinyl)aminomethylenediphosphonate;
tetraethyl N-[2-(2-pyridyl)ethyl]-N-methyl-aminomethylenediphosphonate;
tetraethyl N-(2-pyridyl)-N-(benzyl)-aminomethylenediphosphonate;
tetraethyl N-(2-pyridyl)-N-(p-methoxybenzyl)-aminomethylenediphosphonate;
tetraethyl N-(2-pyridyl)-N-(n-pentyl)-aminomethylenediphosphonate; and
tetraethyl N-(2-pyridyl)-N-(4-hydroxy-3-methoxy-5-methylbenzyl)-aminomethylenediphosphonate.

In some embodiments wherein the modulation of apoE levels are decreased, the compound of formula (1) is selected from the group consisting of:
tetraisopropyl N-(2-pyridyl)aminomethylenediphosphonate;
tetraethyl N-(3-pyridylmethyl)aminomethylenediphosphonate;
tetraethyl N-(2-pyrazinyl)aminomethylenediphosphonate;
tetraethyl N-(2-benzothiazolyl)aminomethylenediphosphonate;
tetraethyl N-(2-pyridyl)-N-methyl-aminomethylenediphosphonate; and
tetraethyl N-(2-pyridylmethyl)aminomethylenediphosphonate.

Wherein the levels of apoE are increased, the method provides that the patient may be suffering from atherosclerosis, Alzheimer's disease, macular degeneration, retinitis pigmentosa, stroke, xanthoma, xanthelasma or degenerative neuropathy, wherein the latter may be associated with diabetic neuropathy or multiple sclerosis.

Other aspects of the present invention provide for methods for elevating high density cholesterol, preventing and/or treating atherosclerosis, preventing and/or treating macular degeneration and retinitis pigmentosa, preventing and/or treating stroke, prevention of degenerative neuropathy, comprising administration of an effective amount of a compound of formula (I) as described above.

Embodiments wherein the levels of apoE are decreased include wherein the patient expresses apoE4, apoE Leiden or a non-functional mutant form of apoE and when the patient is suffering from atherosclerosis or Alzheimer's disease.

A further aspect of the invention provides for a method for the prevention and/or treatment of Alzheimer's disease or dementia comprising administration of an effective amount of a compound of formula (1) as described above. In embodiments wherein the patient is heterozygous or homozygous for apoE2 and/or apoE3, the method provides for the administration of an effective amount of a compound of formula (I) wherein the apoE levels are increased. In embodiments wherein the patient is heterozygous or homozygous for apoE4, the method provides for the administration of an effective amount of a compound of formula (I) wherein the apoE levels are decreased.

The present invention also encompasses a screening method for identifying apoE modulators comprising the combination of an in vitro assay and an in vivo test model that enables the identification of apoE modulators active in a wide range of tissues and in different species. The screening method comprises: (1) testing a compound in vitro for inhibiting or inducing the secretion of apoE in a cell line such as: (a) a monocyte-macrophage cell line such as the THP-1 cell line; (b) a liver derived cell line such as the HepG2 cell line; (c) an intestinal derived cell line such as the CaCo2 cell line; or (d) a brain derived cell line such as the astrocytoma CCF-STTG1 cell line; and (2) testing said compound in vivo in the rat to measure its modulating effect on plasma apoE. The observed increase in plasma apoE has been statistically correlated with an increase in High Density Lipoprotein cholesterol (HDLc, "the good cholesterol"), further confirming the usefulness of this screening system.

DETAILED DESCRIPTION OF THE INVENTION

I. Aminodiphosphonate Compounds

The present invention relates to novel aminodiphosphonate compounds of formula (I) that modulate apoE levels and are useful as agents for the treatment of a number of disorders including cardiovascular and neurological disease states.

In relation to the compounds of formula (I), by "aryl" is meant one optionally substituted 5-, 6-, or 7-membered aromatic ring optionally attached to one optionally substituted 5-, 6-, or 7-membered aromatic or non-aromatic ring, wherein the required first 5-, 6-, or 7-membered aromatic ring is a carbocyclic aromatic ring or a heteroaryl ring containing up to three heteroatoms selected from nitrogen, oxygen or sulfur and wherein the optional second 5-, 6-, or 7-membered aromatic or non-aromatic ring may be carbocycilc or contain up to three hetero atoms selected from nitrogen, oxygen or sulfur. Examples of aryl groups include phenyl, naphthyl, pyridyl, pyrimidinyl, pyrazinyl, pyridazinyl, thiazolyl, thiadiazolyl, furanyl, benzothiazolyl, isoxazolyl, pyrazolyl, triazinyl, imidazolyl, isoquinolinyl, and quinolinyl. These aryl groups may be unsubstituted or substituted by up to seven substituents (for napthyl), six subtituents (isoquinolinyl, and quinolinyl), five subtituents (phenyl), four substituents (for pyridyl and benzothiazolyl), three substituents (pyrimidyl, pyrazinyl, pyridazinyl, pyrazolyl), two substituents (thiazolyl, isoxazolyl, triazinyl and imidazolyl) or one substituent (thiadiazolyl). The substituents may be the same or different and selected from straight or branched $C_1$–$C_8$ alkyl or alkoxy, hydroxy, hydroxymethyl, halogen (fluror, chloro, bromo or iodo), nitro or —$NR^3R^4$, where $R^3$ and $R^4$ are independently selected from hydrogen or $C_1$–$C_4$ alkyl. Examples of substituted aryl groups include ethylpyridyl, methoxypyridyl, dimethylpyridyl, methylpyrimidinyl, dimethylpyrimidinyl, trimethylpyrazoyl, methylisoxazolyl, methylthiazolyl.

Wherein B is a phenyl group, it may be optionally substituted with up to five substituents independently selected from $C_1$–$C_8$ alkyl, $C_1$–$C_8$ alkoxy, hydroxy, halogen or cyano. Examples include phenyl, 4-methoxyphenyl, 4-methylphenyl, 4-hydroxyphenyl, 4-chlorophenyl, 3-hydroxy-4-methoxyphenyl, 4-hydroxy-3-methoxyphenyl, 4-hydroxy-3-methoxy-5-methylphenyl, 3,5-dimethoxy-4-hydroxyphenyl, 3,5-dimethyl-4-hydroxyphenyl, 3-ethoxy-4-hydroxy-5-methylphenyl, 3,4,5-trimethoxyphenyl and 4,5-dimethoxy-3-hydroxyphenyl.

Where substituents of the compounds of formula (I) include $C_1$–$C_8$ alkyl groups, examples include methyl, ethyl, propyl, butyl, pentyl, hexyl, heptyl and octyl groups. Propyl groups may be n-propyl or isopropyl and butyl groups include n-butyl, s-butyl and t-butyl. Examples of $C_1$–$C_8$ alkoxy groups include methoxy, ethoxy, propoxy, butoxy, pentoxy, hexoxy, heptoxy and octoxy groups, a particular example being methoxy. Where a halogen substituent is present, it can be selected from fluorine, chlorine, bromine and iodine. The integers "m" and "n" are the same or different and are integers in the range from 0 to 10, preferably from 0 to 6, particularly 0, 1, 2, 3, 4 and 5. $R^1$ and $R^2$ are independently hydrogen or $C_1$–$C_6$ alkyl. Particular examples of $R^1$ and $R^2$ include methyl, ethyl and propyl, preferably isopropyl.

Pharmaceutically acceptable salts for use in the present invention include those described by Berge et al. (1997), herein incorporated by reference. Such salts may be formed from inorganic and organic acids. Representative examples thereof include maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

Since the compounds of the present invention, in particular compounds of formula (I), are intended for use in pharmaceutical compositions, it will be understood that they are each provided in substantially pure form, for example at least 50% pure, more suitably at least 75% pure, preferably at least 95% pure, and more preferably at least 99% pure (% are on a wt/wt basis). Impure preparations of the compounds of formula (I) may be used for preparing the more pure forms used in the pharmaceutical compositions. Although the purity of intermediate compounds of the present invention is less critical, it will be readily understood that the substantially pure form is preferred as for the compounds of formula (I). Preferably, whenever possible, the compounds of the present invention are obtained in crystalline form.

When some of the compounds of this invention are allowed to crystallise or are recrystallised from organic solvents, solvent of crystallisation may be present in the crystalline product. This invention includes within its scope such solvates. Similarly, some of the compounds of this invention may be crystallised or recrystallised from solvents containing water. In such cases, water of hydration may be formed. This invention includes within its scope stoichiometric hydrates as well as compounds containing variable amounts of water that may be produced by processes such as lyophilisation. In addition, different crystallisation conditions may lead to the formation of different polymorphic forms of crystalline products. This invention includes within its scope all polymorphic forms of the compounds of formula (I).

II. Applications of ApoE Modulators

A. ApoE in Atherosclerosis

As a component of all lipoprotein fractions, apoE plays an important role in cholesterol homeostasis by mediating their interaction with receptors such as the apoB, low-density lipoprotein (LDL) and other specific receptors. The important role of apoE in cardiovascular diseases is demonstrated by the apoE knock-out mouse model, where the animals rapidly develop hypercholesterolemia and atherosclerosis with pathological features similar to human atherosclerosis (Plump, 1997). In addition, the absence of a functional apoE in humans is associated with abnormally high plasma levels of cholesterol and triglycerides and the rapid development of atherosclerosis, notwithstanding a low fat diet (Richard et al., 1995). In the knock-out mouse model, these changes are prevented by infusion of apoE, transplantation of macrophage producing apoE, or gene therapy by introducing the human apoE gene into apoE knock-out mice (Linton et al., 1995). These results indicate a direct beneficial role for apoE and, consequently, a utility for compounds that increase the apoE levels. The aminodiphosphonate compounds of the present invention that increase apoE plasma levels will decrease plasma atherogenic lipoproteins (VLDL, IDL and LDL) by increasing their uptake by the liver. Increasing apoE in HDL will increase the removal of cholesterol from loaded tissues (atherosclerotic arteries) by the reverse cholesterol transport mechanism.

In contrast, hyperlipidemic patients susceptible of developing atherosclerosis due to the expression of a mutated form of apoE, such as apoE Leiden or other variants, should benefit from the treatment with the compounds that decrease apoE production (van Vlijmen et al., 1998; Richard, 1995). Thus, aminodiphosphonate compounds of the present invention that decrease the production of apoE are useful in the prevention and/or treatment of pathological cardiovascular conditions secondary to the presence of non-functional, variants or mutant forms of the apoE molecule.

B. ApoE in the Central Nervous System (CNS)

ApoE also plays a critical role in the CNS. In the brain, apoE is synthesized and secreted by astrocytes, its principal role being cholesterol transport between cells. ApoE is considered to redistribute lipids and to participate in the cholesterol homeostasis of the brain.

ApoE is linked to the neuropathological lesions characteristic of Alzheimer's disease. One isoform, apoE4, is strongly associated with the age of onset of the disease (Poirier, 1994; Rubinsztein, 1995), while another isoform, apoE3, is believed to help maintain healthy microtubules. The increase in both apoE mRNA and the number of astrocytes in the brains of Alzheimer's patients indicates that increased apoE represents an astrocyte repair-mechanism to ameliorate the damage within the nervous cells. Memory deficit, defective repair of brain injury and deposition of the Alzheimer's associated β-amyloid variant $APP^{V717F}$ have been demonstrated in the absence of the apoE gene, i.e., apoE knock out mice (Oitzl et al., 1997; Laskowitz et al., 1997; Walker et al., 1997).

Thus, there is a benefit to increasing apoE production in patients bearing the E2 and E3 isoforms of apoE in regard to the occurrence of Alzheimer's or other spontaneous or traumatic neurological diseases. The aminodiphosphonates of the present invention that increase apoE in the brain will prevent the deposition of plaques associated with Alzheimer's disease and increase the repair mechanism of brain injuries due to mechanical traumas or strokes. Through the increase of neurite extension synaptic sprouting the overall brain activity (i.e. memory) should improve.

Conversely, patients at risk of or suffering from Alzheimer's or spontaneous or traumatic neurological diseases who overexpress the pathological isoforms of apoE, such as apoE4, should benefit from the treatment with a compound that decreases apoE. Thus, aminodiphosphonate compounds of the present invention that decrease the production of apoE are useful in the prevention and/or treatment of the symptomatic and neuropathological cardiovascular conditions characteristic of Alzheimer's or other spontaneous or traumatic neurological diseases that are caused or exacerbated by non-functional, variants or mutant forms of the apoE.

C. ApoE in the Peripheral Nervous System (PNS)

The important role of apoE in nerve regeneration in the PNS is demonstrated by the observation that apoE synthesis is dramatically induced when nerves are injured (Poirier, 1994). The maintenance and/or repair of the myelin sheets involves the participation of apoE secreted by support cells such as glial and Schwann cells. Both apoE synthesis and concentration were found to be abnormally low in degenerative diseases of nervous tissues such as in multiple sclerosis (Gaillard, 1996). ApoE is also considered to stabilize the cytoskeleton apparatus and support neurite elongation, thus having a major effect on the development and remodeling following injury of the nervous system occurring late in life. Thus, the compounds of the present invention that increase apoE will support and increase the speed of the healing process of traumatized nerves (nerve section, crush, etc.) and the prevention and/or healing of degenerative nerves (e.g., multiple sclerosis).

D. ApoE as Modulators of the Immune System

ApoE affects the immune system by acting on lymphocyte proliferation. Furthermore apoE knock out mice are highly sensitive to bacterial infection due to a defect in the innate immune system, suggesting that increasing apoE production should augment the immune response (Roselaar & Daugherty, 1998). Increasing apoE production by utilization of compounds of the present invention should augment ameliorate the immune response in patients in need thereof.

E. Skin Lipid Metabolism Disorders

Lipid homeostasis is well controlled in epithelial cells such as keratinocytes, wherein exported lipids are important for corneocyte adhesion and for forming the cutaneous barrier to the external environment. Excess cholesterol deposition in skin (xanthomas and xanthelasmas) will be prevented by utilization of aminodiphosphonates compounds of the present invention that increase the level of cutaneous apoE.

II. Formulations and Administration

The compounds of formula (I) can be administered by any of a variety of routes. Thus, for example, they can be administered orally, or by delivery across another mucosal surface (for example across the nasal, buccal, bronchial or rectal mucosa), transdermally, or by injection (for example intradermal, intraperitoneal, intravenous or intramuscular injection).

When the compounds are intended for oral administration, they can be formulated, for example, as tablets, capsules, granules, pills, lozenges, powders, solutions, emulsions, syrups, suspensions, or any other pharmaceutical form suitable for oral administration. Oral dosage forms can, if desired, be coated with one or more release delaying coatings to allow the release of the active compound to be controlled or targeted at a particular part of the enteric tract.

Tablets and other solid or liquid oral dosage forms can be prepared (e.g., in standard fashion) from the compounds of formula (I) and a pharmaceutically acceptable solubilizer, diluent or carrier. Examples of solubilizers, diluents or carriers include sugars such as lactose, starches, cellulose and its derivatives, powdered tracaganth, malt, gelatin, talc, stearic acid, magnesium stearate, calcium sulfate, vegetable oils, polyols such as glycerol, propyleneglycol and polyethyleneglycols, alginic acids and alginates, agar, pyrogen free water, isotonic saline, phosphate buffered solutions, and optionally other pharmaceutical excipients such as disintegrants, lubricants, wetting agents such as sodium lauryl sulfate, coloring agents, flavoring agents and preservatives, etc.

Capsules can be of the hard or soft variety and can contain the active compound in solid, liquid or semisolid form. Typically such capsules are formed from gelatin or an equivalent substance and can be coated or uncoated. If it is desired to delay the release of the active compound until the capsule has passed through the stomach and into the intestine, the capsule can be provided with a pH sensitive coating adapted to dissolve at the pH found in the duodenum or ileum. Examples of such coatings include the Eudragits, the uses of which are well known.

Formulations for injection will usually be made up of the appropriate solubilizers such as detergents which may also include compounds and excipients such as buffering agents to provide an isotonic solution having, the correct physiological pH. The injectable solutions are typically pyrogen-free and can be provided in sealed vials or ampoules containing a unit dose of compound.

A unit dosage form of the compounds of the invention typically will contain from 0.1% to 99% by weight of the active substance, more usually from 5% to 75% of the active substance. By way of example, a unit dosage form can contain from 1 mg to 1 g of the compound, more usually from 10 mg to 500 mg, for example between 50 mg and 400 mg, and typically in doses of 100 mg to 200 mg.

The compounds of the invention will be administered in amounts which are effective to provide the desired therapeutic effect. The concentrations necessary to provide the desired therapeutic effect will vary according to among other things the precise nature of the disease, the size, weight and age of the patient and the severity of the disease. The doses administered will preferably be non-toxic to the patient, although in certain circumstances the severity of the disease under treatment may necessitate administering an amount of compound that causes some signs of toxicity.

Typically, the compounds of the invention will be administered in amounts in the range 0.01 mg/kg to 100 mg/kg body weight, more preferably 0.1 mg/kg to 10 mg/kg body weight and particularly 1 mg/kg to 5 mg/kg body weight. For an average human of 70 kg weight, a typical daily dosage of the compounds of the invention would be in the range of 70 mg to 700 mg. Such a dosage can be administered, for example from two to four times daily. Ultimately however, the size of the doses administered and the frequency of administration will be at the discretion and judgment of the physician treating the patient.

For therapeutic use the compounds of the present invention will generally be administered in a standard pharmaceutical composition obtained by admixture with a pharmaceutical carrier selected with regard to the intended route of administration and standard pharmaceutical practice. For example, they may be administered orally in the form of tablets containing such excipients as starch or lactose, or in capsule, ovules or lozenges either alone or in admixture with excipients, or in the form of elixirs or suspensions containing flavoring or coloring agents. They may be injected parenterally, for example, intravenously, intramuscularly or subcutaneously. For parenteral administration, they are best used in the form of a sterile aqueous solution that may contain other substances, for example, enough salts or glucose to make the solution isotonic with blood. The choice of form for administration as well as effective dosages will vary depending, inter alia, on the condition being treated. The choice of mode of administration and dosage is within the skill of the art.

The compounds of formula (I) and their pharmaceutically acceptable salts which are active when given orally can be formulated as liquids, for example syrups, suspensions or emulsions or as solids for example, tablets, capsules and lozenges. A liquid formulation will generally consist of a suspension or solution of the compound or pharmaceutically acceptable salt in suitable liquid carrier(s) for example, ethanol, glycerine, non-aqueous solvent, for example polyethylene glycol, oils, or water with a suspending agent, preservative, flavoring or coloring agents. A composition in the form of a tablet can be prepared using any suitable pharmaceutical carrier(s) routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of formula (I) or a pharmaceutically acceptable salt thereof which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule. Each dosage unit for oral administration contains preferably from 1 to 250 mg (and for parenteral administration contains preferably from 0.1 to 25 mg) of a compound of the structure (I) or a pharmaceutically acceptable salt thereof calculated as the free base.

The pharmaceutically acceptable compounds of the invention will normally be administered to a subject in a daily dosage regimen. For an adult patient this may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the structure (I) or a pharmaceutically acceptable salt thereof calculated as the free base, the compound being administered 1 to 4 times per day.

Disease states which could benefit from increasing plasma and tissue apoE levels include, but are not limited to: atherosclerosis, neurodegenerative disorders such as Alzheimer's disease or dementia. The compounds of this invention modulate apoE and are therefore of value in the treatment of any of these conditions.

Compounds of the present invention may also be of use in preventing and/or treating the above-mentioned disease states in combination with anti-hyperlipidaemic, anti-atherosclerotic, anti-diabetic, anti-anginal, anti-inflammatory or anti-hypertension agents. Examples of the above include cholesterol synthesis inhibitors such as statins, for instance atorvastatin, simnvastatin, pravastatin, cerivastatin, fluvastatin, lovastatin and ZD 4522 (also referred to as S-4522, Astra Zeneca), anti-oxidants such as probucol, insulin sensitisers such as a PPAR gamma activator, for instance G1262570 (Glaxo Wellcome) and the glitazone class of compounds such as rosiglitazone (Avandia, SmithKline Beecham), troglitazone and pioglitazone, calcium channel antagonists, and anti-inflammatory drugs such as NSAIDs.

IV. Synthesis of Aminodiphosphonate Compounds

The preparation of various diphosphonate derivatives are disclosed in U.S. Pat. Nos. 5,624,917, 5,865,314 and 5,624,917, all herein incorporated by reference. The present invention also provides for the preparation of aminodiphosphonate derivatives of the formula (I) where $R^1$, $R^2$, $R^3$ and $R^4$ are the same and depicted as R in formula (Ia):

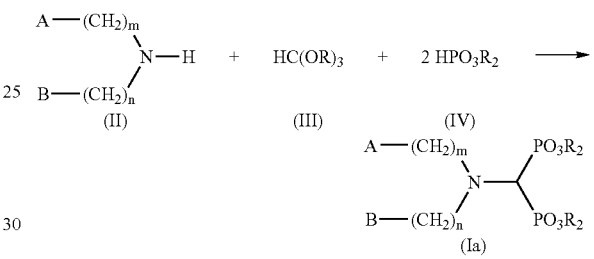

The experimental procedure for preparing compounds (Ia) consists in heating a mixture of the appropriate amine of formula (II) with a trialkyl orthoformate of formula (III) and a dialkyl phosphite of formula (IV). The stoichiometry of the reaction requires a molar ratio of compounds (II):(III):(IV)= 1.0:1.0:2.0, but in practice the reaction proceeds best when 1 equivalent of the amine is dissolved in a slight excess of trialkyl orthoformate III (1.5–2 equivalents) and a larger excess of dialkyl phosphite IV (3–10 equivalents) and the reaction mixture is heated to a temperature above the boiling point of the alcohol formed. The reaction time varies between ca 15 min and 24 h and depends on the extent of formation of the desired compound (Ia) which can be monitored by the analytical methods well known in the art such as thin layer chromatography or gas chromatography.

V. Determination of Biological Activity

The aminodiphosphonates of the invention can modulate (increase or decrease) the apoE production in vitro and in vivo both in plasma and in tissues. The activities of the compounds can be determined using a screening system comprising a combination of an in vitro assay and an in vivo test model that allows the identification of apoE modulators active in a wide range of tissues and in different species. The in vitro assay comprises subjecting a test compound to a first in vitro assay for determining the effect of the test compound in modulating the secretion of apoE by an apoE secreting cell line (e.g., a monocyte-macrophage cell line such as the THP-1 cell line, a liver derived cell line such as the HepG2 cell line, an intestinal derived cell line such as the CaCo2 cell line, or a brain derived cell line such as the astrocytoma CCF-STTG1 cell line; and (2) testing said compound in vivo in the rat to measure its modulating effect on plasma apoE.TBP-1 or HepG2 cells), and selecting a test compound found to have apoE modulating activity of a predetermined level in the first assay and subjecting the compound to a second in vivo assay comprising administering the test compound to a test animal (such as a rat), and determining plasma levels of apoE in the test animal relative to a control.

EXAMPLES OF THE INVENTION

Without further elaboration, it is believed that one skilled in the art can, using the preceding description, utilize the present invention to its fullest extent. The following specific examples are intended merely to illustrate the invention and not to limit the scope of the disclosure or the scope of the claims in any way whatsoever.

Example 1

Tetraethyl N-(2-pyridyl)aminomethylenediphosphonate

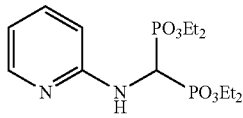

2-Aminopyridine (22 g, 234 mmol), triethylorthoformate (52 g, 351 mmol) and diethyl phosphite (64.5 g, 467 mmol) were combined in a flask equipped with a condenser and heated to 120° C. for 90 min. Heating was discontinued and the ethanol formed was distilled off. The reaction mixture was further concentrated at reduced pressure and the oily residue was purified by column chromatography (silica gel, $CH_2Cl_2$/MeOH 95/5). The purified fractions were concentrated and triturated with petroleum ether to give 54 g (61%) of a solid, mp=63–66° C.

FTIR ($cm^{-1}$): 3436 and 3264: N—H, 1251: (P=O), 1025 and 978: P—O—C

MS (m/e)=380: $M^+$, 243 (100%): $M^+$-$PO_3Et_2$

NMR ($CDCl_3$): δ=8.10, 7.41, 6.63 and 6.51 (4m, 1H each): aromatic H, 2-pyridyl 5.54 (dt, J=10 and 22.5 Hz, 1H): C$\underline{H}$P$_2$ 4.81 (broad d, J=10 Hz, 1H): N—$\underline{H}$ 4.25–4.10 (m, 4H): P—O—C$\underline{H}_2$—CH$_3$ 1.26 and 1.24 (2t, J=7 Hz, 6H): P—O—CH$_2$—C$\underline{H}_3$

Example 2

Tetramethyl N-(2-pyridyl)aminomethylenediphosphonate

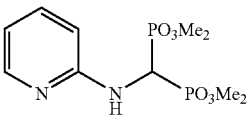

A mixture of 2-aminopyridine (20 g, 210 mmol), trimethylorthoformate (33.8 g, 318 mmol) and dimethyl phosphite (39 ml, 46.8 g, 420 mmol) were combined in a flask equipped with a condenser and heated to 80° C. for 90 min. The condenser was removed to allow the removal of methanol formed, and while the reaction temperature was maintained at 80° C., dimethyl phosphite was added every 2 h in four portions of ca 39 ml each. The reaction mixture was kept at 80° C. for a further 8 h period then was left to stir overnight at room temperature. The precipitate formed was collected by filtration and purified by column chromatography (silica gel, $CH_2Cl_2$/MeOH 95/5) to yield 16 g (23%) of a white solid, mp=162–164° C.

MS (m/e)=324: $M^+$, 215: $M^+$-$PO_3Me_2$, 79: pyridine (100%)

NMR ($CDCl_3$): δ=8.11, 7.43, 6.66 and 6.53 (4m, 1H each): aromatic H, 2-pyridyl 5.66 (dt, J=10 and 22.5 Hz, 1H): C$\underline{H}$P$_2$ 4.86 (broad d, J=10 Hz, 1H): N—$\underline{H}$ 3.85–3.77 (2m, 6H total): P—O—C$\underline{H}_3$

Example 3

Tetraethyl N-(2-pyrazinyl)aminomethylenediphosphonate

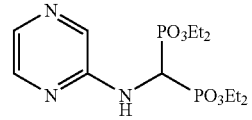

2-Aminopyrazine (4.0 g, 42 mmol), triethylorthoformate (18.7 g, 126 mmol) and a catalytic amount (ca 2 mg) of p-toluenesulfonic acid monohydrate was combined in a flask equipped with a condenser and heated to 120° C. for 15 min. Diethyl phosphite (29.0 g, 210 mmol) was added and the resulting mixture was maintained at 120° C. for 5 h. An additional amount of diethyl phosphite (5.8 g) was added and the reaction was kept at 120° C. for two more hours. Heating was discontinued and the ethanol formed was distilled off. The reaction mixture was further concentrated at reduced pressure and the oily residue was purified by column chromatography (silica gel, $CH_2Cl_2$/MeOH 90/10). The purified fractions were concentrated and triturated with petroleum ether to give 8.6 g (53%) of a solid, mp=56–59° C.

FTIR ($cm^{-1}$): 3506 and 3260: N—H, 1249: (P=O), 1048, 1020 and 985: P—O—C

MS (m/e)=381: $M^+$, 244 (100%): $M^+$-$PO_3Et_2$

NMR ($CDCl_3$): δ 8.06, 8.01 and 7.89 (3m, 1H each): aromatic H, pyrazine 5.36 and 5.32 (partially overlapped peaks, 2H total): C$\underline{H}$P$_2$ and N—$\underline{H}$ 4.25–4.10 (m, 4H total): P—O—C$\underline{H}_2$—CH$_3$ 1.28 and 1.25 (2t, J=7 Hz, 6H): P—O—CH$_2$—C$\underline{H}_3$

Example 4

Tetraethyl N-(2-pyridyl)-N-methyl-aminomethylenediphosphonate

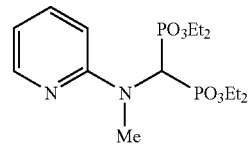

A mixture of 2-(methylamino)pyridine (3.0 ml, 29.2 mmol), triethylorthoformate (5.8 ml, 34.9 mmol) and diethyl phosphite (11.4 ml, 88.5 mmol) was heated to 150° C. for 16 h in a flask equipped with a condenser. Another portion of diethyl phosphite (7.5 ml, 58.2 mmol) was added and the reaction was heated at 150° C. for a further 7 h. Heating was discontinued, the ethanol formed was distilled off and the reaction mixture was further concentrated at reduced pressure. The residue was submitted to column chromatography (silica gel, $CH_2Cl_2$/MeOH 95/5) and the purified fractions gave 2.3 g (19%) of an oil.

FTIR ($cm^{-1}$): 1258: (P=O), 1027 and 972: P—O—C

MS (m/e)=394: $M^+$, 257 (100%): $M^+$-$PO_3Et_2$

NMR ($CDCl_3$): δ=8.12, 7.5 1and 6.62 (4m, 1H each): aromatic H, 2-pyridyl 6.61 (overlapped t, J=26 Hz, 1H): C H̲$P_2$ 4.24–4.09 (m, 4H total): P—O—C H̲$_2$—$CH_3$ 3.24 (s, 1H): N-M̲e 1.24 and 1.23 (2t, J=7 Hz, 6H): P—O—$CH_2$—C H̲$_3$

Example 5

Tetraethyl N-[2-(2-pyridyl)ethyl]-N-methyl-aminomethylenediphosphonate

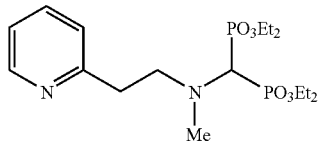

2-(2-Methylaminoethyl)pyridine (1.50 ml, 10.8 mmol), triethylorthoformate (2.0 ml, 12.0 mmol) and diethyl phosphite (5.20 ml, 40.3 mmol) were combined in a flask equipped with a condenser and heated to 120° C. for 2 h. The reaction mixture was concentrated at reduced pressure and the oily residue was purified by two column chromatographies (silica gel, $CH_2Cl_2$/MeOH 95/5 then AcOEt/MeOH 8/2) to give 2.0 g (44%) of an oil.

FTIR ($cm^{-1}$): 1249: (P=O), 1028 and 970: P—O—C

MS (m/e)=422: $M^+$, 285: $M^+$-$PO_3Et_2$, 135 (100%): $M^+$+1-$CH_2(PO_3Et_2)_2$

NMR ($CDCl_3$): δ=8.51, 7.59, 7.22 and 7.10 (4m, 1H each): aromatic H, 2-pyridyl 4.25–4.05 (m, 4H total): P—O—$CH_2$—$CH_3$ 3.50 (t, J=25 Hz, 1H): C H̲$P_2$ 3.22 and 2.96 (2 broad t, J=7 Hz): Pyridyl-(C H̲$_2$)$_2$ 2.71 (broad s, 1H): N-M̲e 1.31 (dt, J=7 Hz, 6H): P—O—$CH_2$—$CH_3$

Example 6

Tetraethyl N-(2-pyridyl)-N-(n-pentyl)-aminomethylenediphosphonate

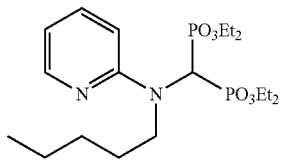

Acetic acid was added dropwise to 100 ml of a methanol solution containing 2-aminopyridine (3.0 g, 31.9 mmol), valeraldehyde (4.4 ml, 41.7 mmol) and a crystal of Neutral Red until the solution becomes red. After 15 min, a solution of 4.9 g sodium cyanoborohydride in 20 ml MeOH was added and the mixture was stirred at room temperature overnight. Another portion of sodium cyanoborohydride (0.5 g) was added and the mixture was stirred for a further 2 h. Water was added to the reaction mixture which was then extracted with dichloromethane. The organic phase was dried, concentrated and the residue was purified by column chromatography (silica gel, $CH_2Cl_2$/MeOH 95/5) to give 4.9 g (95%) of 2-(n-pentylamino)pyridine. A mixture of 2-(n-pentylamino)pyridine (3.39 g, 20.2 mmol), triethylorthoformate (4.0 ml, 24.0 mmol) and diethyl phosphite (13.0 ml, 101 mmol) was heated to 150° C. for 17 h in a flask equipped with a condenser. Heating was discontinued and the reaction mixture was concentrated at reduced pressure. The residue was submitted to several purifications by column chromatography (silica gel, $CHCl_3$/AcOEt 9/1, $CH_2Cl_2$/MeOH 95/5 and $CH_2Cl_2$/AcOEt/MeOH 7/2/1) and the purified fractions gave 1.5 g (17%) of an oil.

FTIR ($cm^{-1}$): 1259: (P=O), 1024 and 972: P—O—C

MS (m/e)=450: $M^+$, 313: $M^+$-$PO_3Et_2$, 163 (100%): $M^+$+1-$CH_2(PO_3Et_2)_2$

NMR (DMSO): δ=8.10, 7.59 and 6.67 (4m, 1H each): aromatic H, 2-pyridyl 6.38 (t, J=26 Hz, 1H): C H̲$P_2$ 4.10–3.92 (m, 4H total): P—O—C H̲$_2$—$CH_3$ 3.48 (broad t, 1H): N—C H̲$_2$ 1.64 and 1.29 (2m, 4H): N—$CH_2$—(C H̲$_2$)$_2$ 1.14 and 1.08 (2t, J=7 Hz, 6H): P—O—$CH_2$—C H̲$_3$ 0.88 (t, J=7 Hz, 3H): N—$(CH_2)_3$—$CH_3$

Example 7

Tetraethyl N-(2-pyridyl)-N-(p-methoxybenzyl)-aminomethylenediphosphonate

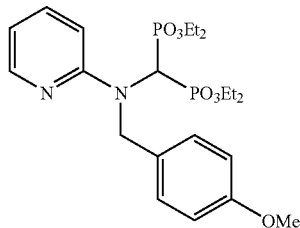

A mixture of 2-(4-methoxybenzylamino)pyridine (3.03 g, 14.1 mmol), triethylorthoformate (2.8 ml, 16.8 mmol) and diethyl phosphite (9.0 ml, 70 mmol) was heated to 150° C. for 24 h in a flask equipped with a condenser. Heating was discontinued and the reaction mixture was concentrated at reduced pressure. The residue was submitted to a column chromatography (silica gel, $CH_2Cl_2$/MeOH 95/5) to give 1.5 g (20%) of an oil.

FTIR ($cm^{-1}$): 1256: (P=O), 1029 and 971: P—O—C

MS (m/e)=500: $M^+$, 213 (100%): $M^+$+1-$CH_2(PO_3Et_2)_2$

NMR ($CDCl_3$): δ=8.15, 7.31, 6.61 and 6.33 (4m, 1H each): aromatic H, 2-pyridyl 7.25 and 6.82 (2 m, 4H): aromatic H, phenyl 6.88 (t, J=26 Hz, 1H): C H̲$P_2$ 4.84 (s, 1H): N—C H̲$_2$-phenyl 4.25–4.04 (m, 4H total): P—O—C H̲$_2$—$CH_3$ 3.77 (s, 3H): phenyl-OM̲e 1.23 and 1.15 (2t, J=7 Hz, 6H): P—O—$CH_2$—C H̲$_3$

Example 8

Tetraethyl N-(2-pyridylmethyl)aminomethylenediphosphonate

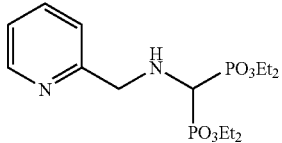

A mixture of 2-pyridinecarboxaldehyde (1.23 g, 11.5 mmol), tetraethyl aminomethylenediphosphonate (3.0 g, 9.9 mmol) and a catalytic amount of p-toluenesulfonic acid dissolved in 10 ml toluene was heated to reflux for 7 h. Toluene was evaporated and the residue dissolved in ethanol was submitted for 12 h to catalytic hydrogenation with 10% palladium on charcoal. Ethanol was evaporated and the title compound was obtained as an oil (1.30 g, 33%) by column chromatography (silica gel, $CH_2Cl_2$/MeOH 9/1).

FTIR ($cm^{-1}$): 3454: N—H, 1249: (P=O), 1026 and 973: P—O—C

MS (m/e)=394: $M^+$, 257: $M^+$-$PO_3Et_2$, 93 (100%): Pyridine-$CH_3$

NMR ($CDCl_3$): δ=8.54, 7.66, 7.44 and 7.18 (4m, 1H each): aromatic H, 2-pyridyl 4.27–4.17 (m, 4H total): P—O—C$\underline{H}_2$—$CH_3$ 4.19 (broad s, 2H): N—C$\underline{H}_2$ 3.44 (t, J=22 Hz, 1H): C$\underline{H}P_2$ 1.34 (t, J=7 Hz, 6H): P—O—$CH_2$—C$\underline{H}_3$

Example 9

Tetraethyl N-(3-pyridylmethyl)aminomethylenediphosphonate

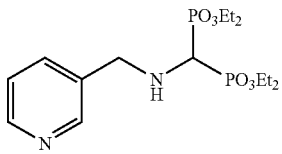

A mixture of 3-pyridinecarboxaldehyde (2.7 g, 25.3 mmol), tetraethyl aniinomethylenediphosphonate (8.03 g, 26.5 mmol) dissolved in 60 ml ether was reacted at room temperature for 14 h. Ether was evaporated and the residue dissolved in ethanol was submitted for 12 h to catalytic hydrogenation with 10% palladium on charcoal. Ethanol was evaporated and the title compound was obtained as an oil (3.12 g, 29%) by column chromatography (silica gel, $CH_2Cl_2$/MeOH 9/1).

MS (m/e)=394: $M^+$, 257: $M^+$-$PO_3Et_2$, 92 (100%): Pyridine-$CH_2$

NMR ($CDCl_3$): δ=8.59, 8.52, 7.73 and 7.27 (4m, 1H each): aromatic H, 3-pyridyl 4.27–4.17 (m, 4H total): P—O—C$\underline{H}_2$—$CH_3$ 4.09 (broad s, 2H): N—C$\underline{H}_2$ 3.26 (t, J=21 Hz, 1H): C$\underline{H}P_2$ 1.36 (2t, J=7 Hz, 6H): P—O—$CH_2$—C$\underline{H}_3$

Example 10

Tetraisopropyl N-(2-pyridyl)aminomethylenediphosphonate

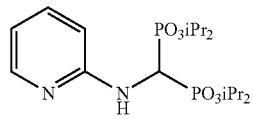

2-Aminopyridine (3.0 g, 32 mmol), triisopropylorthoformate (9.10 g, 48 mmol) and diisopropyl phosphite (10.6 g, 64 mmol) were combined in a flask equipped with a condenser and heated to 120° C. for 5 h. Heating was discontinued and the isopropanol formed was distilled off. The reaction mixture was further concentrated at reduced pressure and the oily residue was purified by column chromatography (silica gel, $CH_2Cl_2$/MeOH 95/5). The purified fractions were concentrated and triturated with petroleum ether to give 10.7 g (77%) of a solid, mp 98–100° C.

MS (m/e)=436: $M^+$, 271: $M^+$-$PO_3iPr_2$, 187 (100%)

NMR ($CDCl_3$): δ=8.09, 7.41, 6.61 and 6.51 (4m, 1H each): aromatic H, 2-pyridyl 5.37 (dt, J=10 and 22.5 Hz, 1H): C$\underline{H}P_2$ 4.86 (broad d, J=10 Hz, 1H): N—$\underline{H}$ 4.82–4.72 (m, 4H): P—O—C$\underline{H}$—$(CH_3)_2$ 1.32, 1.28, 1.24 and 1.18 (4t, J=7 Hz, 6l): P—O—CH—$(C\underline{H}_3)_2$

Example 11

Tetraethyl N-(3-pyridyl)aminomethylenediphosphonate

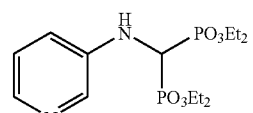

3-Aminopyridine (3.0 g, 32 mmol), triethylorthoformate (7.1 g, 48 mmol) and diethyl phosphite (13.2 g, 96 mmol) were combined in a flask equipped with a condenser and heated to 120° C. for 3 h. Heating was discontinued and the ethanol formed was distilled off. The reaction mixture was further concentrated at reduced pressure and the oily residue was purified by two column chromatography runs (silica gel, $CH_2Cl_2$/MeOH 95/5). The purified fractions were concentrated to give 1.1 g (10%) of an oil.

FTIR ($cm^{-1}$): 3436 and 3264: N—H, $^{125}$I: (P=O), 1025 and 978: P—O—C

MS (m/e)=380: $M^+$, 243 (100%): $M^+$-$PO_3Et_2$

NMR ($CDCl_3$): δ=8.12, 8.04, 7.12 and 7.0 (4m, 1H each): aromatic H, 3-pyridyl 4.26–4.10 (m and other peaks): P—O—$CH_2$—C$\underline{H}_3$, C$\underline{H}P_2$ and N—$\underline{H}$ 1.31 and 1.26 (2t, J=7 Hz, 6H): P—O—$CH_2$—C$\underline{H}_3$

Example 12

Tetraethyl N-[3-(2,6-dimethylpyridyl)]aminomethylene diphosphonate

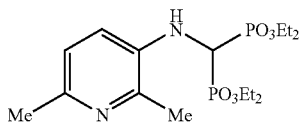

3-Amino-2,6-dimethylpyridine (5.0 g, 41 mmol), triethylorthoformate (9.1 g, 61 mmol) and diethyl phosphite (16.9 g, 122 mmol) were combined in a flask equipped with a condenser and heated to 120° C. for 5 h. Heating was discontinued and the excess of diethyl phosphite and the ethanol formed were distilled off. The reaction mixture was further concentrated at reduced pressure and the oily residue was purified by two column chromatography runs (silica gel, $CH_2Cl_2$/MeOH 95/5). The purified fractions were concentrated to give 8.6 g (52%) of an oil.

FTIR ($cm^{-1}$): 3436: N—H, 1253: (P=O), 10215 and 974: P—O—C

MS (m/e)=408: $M^+$, 271 (100%): $M^+$-$PO_3Et_2$

NMR ($CDCl_3$): δ=6.9 (m, 2H): aromatic H, 3-pyridyl 4.26–4.12 and 4.10–3.95 (m and other peaks): P—O—CH$_2$—CH$_3$, CHP$_2$ and N—H 2.45 and 2.43(2s, 3H each): Pyridine-CH$_3$ 1.29 and 1.27 (2t, J=7 Hz, 6H): P—O—CH$_2$—CH$_3$

Example 13

Tetraethyl N-(3-quinolinyl)aminomethylenediphosphonate

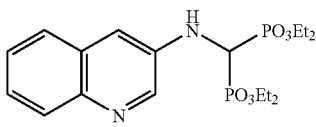

3-Aminoquinoline (4.0 g, 28 mmol), triethylorthoformate (6.17 g, 42 mmol) and diethyl phosphite (11.5 g, 83 mmol) were combined in a flask equipped with a condenser and heated to 120° C. for 7 h. Heating was discontinued and the ethanol formed and excess of diethyl phosphite were distilled off. The reaction mixture was further concentrated at reduced pressure and the oily residue was purified by two column chromatography runs (silica gel, $CH_2Cl_2$/MeOH 90/10). The purified fractions were concentrated to give 2.8 g (24%) of a solid, mp=156–158° C.

MS (m/e)=430: $M^+$, 293 (100%): $M^+$-$PO_3Et_2$

NMR ($CDCl_3$): δ=8.52, 7.97, 7.64, 7.46 and 7.2 (5m, 6H total): aromatic H, 3-quinolinyl 4.52(m, 1H): N—H 4.3–4.14 (m and other peaks): P—O—CH$_2$—CH$_3$ and CHP$_2$ 1.31 and 1.26 (2t, J=7 Hz, 6H): P—O—CH$_2$—CH$_3$

Example 14

Tetraethyl N-(2-benzothiazolyl)aminomethylenediphosphonate

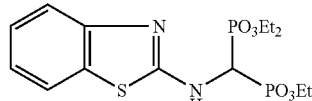

2-Aminobenzothiazole (5.0 g, 33 mmol), triethylorthoformate (7.4 g, 50 mmol) and diethyl phosphite (13.8 g, 100 mmol) were combined in a flask equipped with a condenser and heated to 120° C. for 7 h. Heating was discontinued and the ethanol formed and excess of diethyl phosphite were distilled off. The reaction mixture was further concentrated at reduced pressure and the residue was purified by column chromatography (silica gel, $CH_2Cl_2$/MeOH 95/5). The purified fractions were concentrated and triturated with petroleum ether to give 5.6 g (38%) of a solid, mp=157–162° C.

MS (m/e)=43: $M^+$, 299 (100%): $M^+$-$PO_3Et_2$

NMR ($CDCl_3$): δ=7.58, 7.56, 7.31 and 7.12 (4m, 1H each): aromatic H, benzo ring 5.95 (m, 1H):N—H 4.24 (m, 1H): CHP$_2$ 4.3–4.15 (m, 4H): P—O—CH$_2$—CH$_3$ 1.30 and 1.27 (2t, J=7 Hz, 6H): P—O—CH$_2$—CH$_3$

Example 15

Tetraethyl N-(2-pyridyl)-N-(benzyl)-aminomethylene diphosphonate

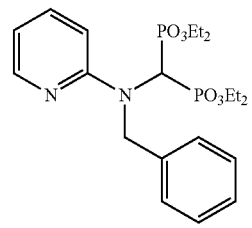

The title compound was obtained in 35% yield as an oil by following the method described in Example 7 and using 2-(benzylamino)pyridine as the amine.

MS (m/e)=470: $M^+$, 183 (100%): $M^+$+1-$CH_2(PO_3Et_2)_2$

NMR (DMSO): δ=8.16, 7.42, 6.67 and 6.28 (4m, 1H each): aromatic H, 2-pyridyl 7.31, 7.26 and 7.18 (3 m, 5H total): aromatic H, phenyl 6.58 (t, J=26 Hz, 1H): CHP$_2$ 4.8 (s, 1H): N—CH$_2$-phenyl 4.1–3.95 (m, 4H total): P—O—CH$_2$—CH$_3$ 1.13 and 1.05 (2t, J=7 Hz, 6H): P—O—CH$_2$—CH$_3$

Example 16

Tetraethyl N-(2-pyridyl)-N-(4-hydroxy-3-methoxy-5-methylbenzyl)-aminomethylenediphosphonate

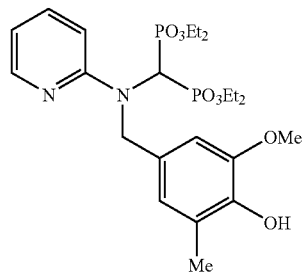

The title compound was obtained in 37% yield as an oil by following the method described in Example 7 and using 2-[(4-hydroxy-3-methoxy-5-methylbenzyl)]aminopyridine as the amine.

FTIR (cm$^{-1}$): 1256: (P=O), 1029 and 971: P—O—C
MS (m/e)=530: M$^+$, 243 (100%): M$^+$+1-CH$_2$(PO$_3$Et$_2$)$_2$
NMR (DMSO): δ=8.15, 7.32, 6.64 and 6.38 (4m, 1H each): aromatic H, 2-pyridyl 6.86 and 6.71: (2 m, 2H total): aromatic H, phenyl 6.91 (t, J=26 Hz, 1H): C$\underline{H}$P$_2$ 5.3 (s, 1H): O$\underline{H}$ 4.77 (s, 1H): N—C$\underline{H}_2$-phenyl 4.25–4.05 (m, 4H total): P—O—C$\underline{H}_2$—CH$_3$ 3.79 (s, 1H): OC$\underline{H}_3$ 2.21 (s, 1H): CH$_3$ 1.21 and 1.18 (2t, J=7 Hz, 6H): P—O—CH$_2$—C$\underline{H}_3$

Example 17

In Vitro Biological Activity (a) Cell Culture

The THP-1 cell line was derived from the peripheral blood of a 1-year-old boy with acute monocytic leukaemia and were obtained from the European Collection of Animal Cell Cultures (ECACC, #88081201). These cells did not express surface and cytoplasmic immunoglobulins; they were phagocytic and differentiated into macrophage-like cells. The cells were grown as non-adherent cells in RPMI 1640 culture medium, 2 mM glutamine, 20 µM 2-mercaptoethanol. Fresh medium was added to maintain cell density between 2 and 9×10$^5$ cells/ml. Once a week, new cultures were initiated by inoculating 10 ml of medium with 2×10$^6$ cells in a 75 cm$^2$ plate. The plates were kept at 37° C. in a 5% CO$_2$ atmosphere. For screening, cells were seeded in 24-well plates at the density of 2×10$^5$ cells per well. Phorbol-12-myristat-13-acetate (PMA) was added at 0 and 5 nM to initiate TBP-1 differentiation into adherent macrophage-like cells. Vehicles, reference compounds and test compounds were added simultaneously at concentrations varying from 50 µM and incubated for 72 hours. The culture medium was then recovered, centrifuged at 300 g for 5 min to remove any unattached cell and stored at −20° C. before analysis.

(b) ApoE Determination by ELISA

Ninety-six well-microtiter plates were coated by incubating with a 5% gelatin solution from porcine skin, bloom 60 in 50 mM carbonate-bicarbonate buffer, pH9.6 at the concentration of 200 µl/well, for 2 hours at 37° C. The coating solution was carefully removed and the sample to be analyzed was added (100 µl/well) at the appropriate dilution. Dilutions of a human apoE standard were simultaneously assayed. Samples and antibodies were diluted in the following buffer solution: PBS, 1% BSA, 0.1% Tween 20, pH 7.4. Samples were incubated for 1 hour at 37° C. and the wells were washed 3 times with 200 µl of buffer solution. One hundred microliters per well of the primary antibody (goat anti-human apoE IgG) diluted 10,000-fold was incubated for 1 hour at 37° C. under continuous shaking. After the third wash, 100 µl/well of the secondary antibody (anti-goat-IgG peroxidase conjugate) diluted 5000 fold was incubated for 1 hour at 37° C. with continuous shaking. Wells were washed 5 times and 100 µl/well of substrate (ortho-phenylenediamine dihydrochloride) was incubated for the appropriate time at room temperature in the dark with continuous shaking. The reaction was stopped by adding 50 µl/well of 3M sulfuric acid and incubating for 1 min. at room temperature. The absorbance at 492 nm versus 620 nm was read on a microplate photometer and the results were then converted in human apoE ng equivalent.

This assay was validated by testing ATRA (all-trans retinoic acid) as reference compound. Test results showed that ATRA decreased the production of apoE by THP-1 cells, which is consistent with the decrease in plasma levels of apoE observed in vivo in the rat. Since ATRA is known to act by regulating the expression of specific genes controlled by nuclear receptors, THP-1 cells can be used as a relevant model to screen compounds affecting the expression of the apoE gene.

Compounds of formula (I) as shown in TABLE 1, wherein m=0, n=0 and R$^1$=R$^2$=R$^3$=R$^4$ were tested for their activity in modulating the secretion of apoE by THP-1 cells in the conditions described above.

TABLE 1

Compounds of formula (I) tested on the secretion of apoE by THP-1 cells

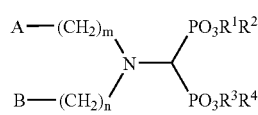

(I)

| Compound | A | m | B | n | R$^1$, R$^2$R$^3$, R$^4$ |
|---|---|---|---|---|---|
| 1 | 2-pyridyl | 0 | H | 0 | CH$_3$— |
| 2 | 2-pyridyl | 0 | H | 0 | CH$_3$CH$_2$— |

TABLE 1-continued

Compounds of formula (I) tested
on the secretion of apoE by THP-1 cells $$A-(CH_2)_m\underset{B-(CH_2)_n}{\overset{}{\diagdown}}N-\underset{PO_3R^3R^4}{\overset{PO_3R^1R^2}{\diagup}} \quad (I)$$

| Compound | A | m | B | n | R$^1$, R$^2$R$^3$, R$^4$ |
|---|---|---|---|---|---|
| 3 | 2-pyridyl | 0 | H | 0 | (CH$_3$)$_2$CH$_2$— |
| 4 | 3-pyridyl | 1 | H | 0 | CH$_3$CH$_2$— |
| 5 | 3-pyridyl | 0 | H | 0 | CH$_3$CH$_2$— |
| 6 | 2,6-dimethyl-3-pyridyl | 0 | H | 0 | CH$_3$CH$_2$— |
| 7 | 2-pyrazinyl | 0 | H | 0 | CH$_3$CH$_2$— |
| 8 | 2-benzothiazolyl | 0 | H | 0 | CH$_3$CH$_2$— |
| 9 | 3-quinolinyl | 0 | H | 0 | CH$_3$CH$_2$— |
| 10 | 2-pyridyl | 0 | H | 1 | CH$_3$CH$_2$— |
| 11 | 2-pyridyl | 2 | H | 1 | CH$_3$CH$_2$— |
| 12 | 2-pyridyl | 0 | phenyl | 1 | CH$_3$CH$_2$— |
| 13 | 2-pyridyl | 0 | 4-methoxyphenyl | 1 | CH$_3$CH$_2$— |

TABLE 1-continued

Compounds of formula (I) tested
on the secretion of apoE by THP-1 cells $$A-(CH_2)_m\diagdown_{N}\diagup^{PO_3R^1R^2}_{PO_3R^3R^4}$$
$$B-(CH_2)_n\diagup \diagdown$$
(I)

| Compound | A | m | B | n | $R^1, R^2 R^3, R^4$ |
|---|---|---|---|---|---|
| 14 | 2-pyridyl | 1 | H | 0 | $CH_3CH_2-$ |
| 15 | 2-pyridyl | 0 | H | 5 | $CH_3CH_2-$ |
| 16 | 2-pyridyl | 0 | 2-MeO, 6-Me, 4-... hydroxyphenyl (MeO, HO, Me substituted phenyl) | 1 | $CH_3CH_2-$ |

Compounds 1, 2, 5, 6, 9, 11, 12, 13, 15 and 16 were found to increase apoE between +28% and +250%. Compounds 3, 4, 7, 8, 10 and 14 were found to apoE secretion between −10 and −22%.

Example 18

In Vivo Biological Activity (a) Rat Model

Rats fed a normal diet are a convenient model recently proposed for the screening of apoE modulating compounds (Leininger-Muller & Siest, 1996, herein incorporated by reference).

This model was validated by testing the hypocholesterolemic drug gemfibrozil (200 mg/kg) as reference compound. The values obtained were comparable to those reported in the literature: apoE was increased by +75% and HDL cholesterol by +42% (200 mg/kg/day for 5 days). Furthermore ATRA (all-trans retinoic acid), which is a potent inhibitor of apoE production by THP-1 cells, was found to decrease plasma level of apoE in rats and to decrease the HDL cholesterol level.

(b) Screening Protocol

Two groups of 4 or 5 OFA rats (Iffa-Credo, France) weighing between 140 g and 160 g were acclimatized for at least one week, allowed UAR food and tap water ad libitum under a 12/12 hours light/obscurity cycle (7.00 am–7.00 pm) then were treated daily between 3.00 pm and 4.00 pm with test compounds (200 mg/kg/day) p.o. in a vehicle volume of 1 ml for 5 days. Test compounds were given as a suspension in 20% Tween-80 supplemented with 0.5% carboxymethylcellulose. The control group received 1 ml vehicle alone. After a treatment period of 5 days, rats were weighed, sacrificed by decapitation under pentobarbital anesthesia after an overnight fast. Blood was collected on EDTA and plasma was used for analysis.

(c) Plasma Analysis

ApoE was quantified by an ELISA method using a goat anti-apolipoprotein E antibody. Briefly, a dilution to 1/200 of rat plasma was coated on microtiter plates. ApoE was recognized by the polyclonal antibody; the conjugate antibody (anti-goat IgG peroxidase) was then added for substrate biochemical recognition. Apolipoprotein E was expressed as % change from mean control value. Cholesterol was measured with a commercially available enzymatic kit. Results were expressed as % change from control group.

(d) Results

Selected compounds of formula (I) were submitted to the in vivo rat test and the results obtained with a series of compounds are provided in the following TABLE 2.

TABLE 2

Effect of Compounds of formula (I) on rat plasma apoE

| Compound | Rat Plasma apoE (% change) |
|---|---|
| 1 | +69 |
| 2 | +44 |
| 3 | +16 |

Compound 2, tetraethyl N-(2-pyridyl)aminomethylene-diphosphonate:

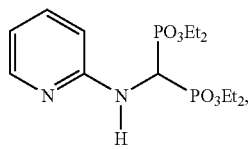

was further tested in a dose-response experiment. Compound 2 was given to OFA rats at the doses of 50, 100, 200 mg/kg p.o for 5 days; the biological values obtained at Day 5 are reported in TABLE 3. Plasma apoE and HDL cholesterol (HDLc) levels were both increased in a dose-response way. Furthermore, the direct and statistically significant correlation observed between plasma apoE and HDLc levels confirms the role played by apoE in plasma HDL concentrations.

TABLE 3

Effect of Compound 2 on rat plasma apoE and HDLc

| Dose of Compound 2 (mg/kg/day) | Rat Plasma apoE (% change) | Rat Plasma HDLc (% change) |
| --- | --- | --- |
| 50 | +38 | +27 |
| 100 | +37 | +34 |
| 200 | +62 | +68 |

The present invention has been shown by both description and examples. The Examples are only examples and cannot be construed to limit the scope of the invention. One of ordinary skill in the art will envision equivalents to the inventive process described by the following claims that are within the scope and spirit of the claimed invention.

REFERENCES

The following references, to the extent that they provide exemplary procedural or other details supplementary to those set forth herein, are specifically incorporated herein by reference.

Berge et al., "Pharmaceutical salts," J. Pharm. Sci., 66:1–19, 1997.
Gaillard, "Apolipoprotein E intrathecal synthesis is decreased in multiple sclerosis patients," Ann. Clin. Biochem., 33:148–150, 1996.
Laskowitz et al., "Apolipoprotein E-deficient mice have increased susceptibility to focal cerebral ischemia," J. Cerebral Blood Flow Metab., 17: 753–758 1997.
Leininger-Muller & Siest, "The rat, a useful model for pharmacological studies on apolipoprotein E," Life Sciences, 58:455–467, 1996.
Linton et al., "Prevention of atherosclerosis in apolipoprotein E-deficient mice by bone marrow transplantation" Science, 267:1034–1037, 1995.
Oitzl et al., "Severe learning deficits in apolipoprotein E knockout mice in a water maze task," Brain Res., 752: 189–196, 1997.
Poirier, "Apolipoprotein E in animal models of CNS injury and in Alzheimer's disease," Trends in Neurosciences 17:525–530, 1994.
Plump, "Atherosclerosis and the mouse—a decade of experience," Annal. Med., 29:193–198, 1997.
Richard et al., "Identification of a new apolipoprotein E variant (E(2) Arg(142)→Leu) in type III hyperlipidemia" Atherosclerosis, 112:19–28, 1995.
Roselaar & Daugherty, "Apolipoprotein E-deficient mice have impaired innate immune responses to listeria monocytogenes in vivo," J. Lipid Res., 39:1740–1743, 1998.
Rubinsztein, "Apolipoprotein E—a review of its roles in lipoprotein metabolism, neuronal growth and repair and as a risk factor for Alzheimner's disease," Psychological Med., 25:223–229, 1995.
Srivastava et al., "Estrogen up-regulates apolipoprotein E (ApoE) gene expression by increasing apoE mRNA in the translating pool via the estrogen receptor alpha-mediated pathway" J. Biol. Chem., 272:33360–33366, 1997.
Stone et al., "Astrocytes and microglia respond to estrogen with increased apoE mRNA in vivo and in vitro" Experimental Neurology, 143:313–318, 1997.
van Vlijmen et al., "Apolipoprotein E*3 Leiden transgenic mice as a test model for hypolipidaemic drugs," Arzneimittel-Forschung, 48:396–402, 1998.
Walker et al., "Cerebral lipid deposition in aged Apolipoprotein E-deficient mice", Am. J. Pathol., 151:1371–1377, 1997.

The invention claimed is:

1. A method of modulating the production of apoE by an apoE producing cell, comprising contacting said apoE producing cell with an effective amount of a compound of formula (I):

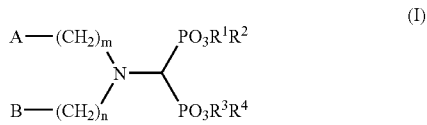

wherein A is an aryl group optionally substituted by one or more substituents independently selected from the group consisting of hydrogen, $C_1$–$C_8$ alkyl, $C_1$–$C_8$ alkoxy, halogen, nitro, amino, and $NR^5R^6$, where $R^5$ and $R^6$ are independently hydrogen or $C_1$–$C_4$ alkyl;

B is hydrogen, $C_1$–$C_8$ alkyl group, or phenyl optionally substituted with one or more substituents independently selected from the group consisting of hydrogen, $C_1$–$C_8$ alkyl, $C_1$–$C_8$ alkoxy, hydroxy, halogen and cyano;

m and n are independently selected are an integer from zero to 10, $R^1$, $R^2$, $R^3$ and $R^4$ are independently hydrogen or $C_1$–$C_6$ alkyl, or a pharmaceutically acceptable salt thereof.

2. The method of claim 1, wherein A is an optionally substituted pyridyl, optionally substituted pyrazinyl, optionally substituted quinolinyl or optionally substituted benzothiazolyl.

3. The method of claim 2, wherein said optionally substituted pyridyl is 2-pyridyl, 3-pyridyl or 3-(2,6-dimethyl pyridyl).

4. The method of claim 2, wherein n is 1 and B is an optionally substituted phenyl group.

5. The method of claim 4, wherein said optionally substituted phenyl group is phenyl, p-methoxyphenyl or 4-hydroxy-3-methoxy-5-methylphenyl.

6. The method of claim 2, wherein n is an integer from 0 to 6 and B is hydrogen.

7. The method of claim 6, wherein n is 0, 1 or 5.

8. The method of claim 1, wherein $R^1$, $R^2$, $R^3$ and $R^4$ are the same and are methyl, ethyl or isopropyl.

9. The method of claim 1, wherein said modulation of the production of apoE by said apoE producing cell comprises increasing the production of apoE by said apoE producing cell.

10. The method of claim 9, wherein said compound of claim 1 is selected from the group consisting of:
tetramethyl N-(2-pyridyl)aminomethylenediphosphonate;
tetraethyl N-(2-pyridyl)aminomethylenediphosphonate;
tetraethyl N-(3-pyridyl)aminomethylenediphosphonate;
tetraethyl N-[3-(2,6-dimethylpyridyl)]aminomethylenediphosphonate;
tetraethyl N-(3-quinolinyl)aminomethylenediphosphonate;
tetraethyl N-[2-(2-pyridyl)ethyl]-N-methyl-aminomethylenediphosphonate;
tetraethyl N-(2-pyridyl)-N-(benzyl)-aminomethylenediphosphonate;
tetraethyl N-(2-pyridyl)-N-(p-methoxybenzyl)-aminomethylenediphosphonate;
tetraethyl N-(2-pyridyl)-N-(n-pentyl)-aminomethylenediphosphonate; and
tetraethyl N-(2-pyridyl)-N-(4-hydroxy-3-methoxy-5-methylbenzyl)-aminomethylenediphosphonate.

11. The method of claim 1, wherein said modulation of the production of apoE by said apoE producing cell comprises decreasing the production of apoE by said apoE producing cell.

12. The method of claim 11, wherein said compound of formula (1) is selected from the group consisting of:
tetraisopropyl N-(2-pyridyl)aminomethylenediphosphonate;
tetraethyl N-(3-pyridylmethyl)aminomethylenediphosphonate;
tetraethyl N-(2-pyrazinyl)aminomethylenediphosphonate;
tetraethyl N-(2-benzothiazolyl)aminomethylenediphosphonate;
tetraethyl N-(2-pyridyl)-N-methyl-aminomethylenediphosphonate; and
tetraethyl N-(2-pyridylmethyl)aminomethylenediphosphonate.

13. A method of modulating apoE levels in a patient in need of such treatment, comprising administration of an effective amount of a compound of formula (I):

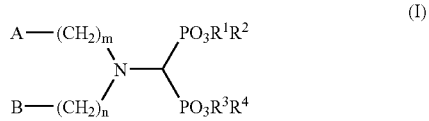

wherein A is an aryl group optionally substituted by one or more substituents independently selected from the group consisting of hydrogen, $C_1$–$C_8$ alkyl, $C_1$–$C_8$ alkoxy, halogen, nitro, amino, and $NR^5R^6$, where $R^5$ and $R^6$ are independently hydrogen or $C_1$–$C_4$ alkyl;
B is hydrogen, $C_1$–$C_8$ alkyl group, or phenyl optionally substituted with one or more substituents independently selected from the group consisting of hydrogen, $C_1$–$C_8$ alkyl, $C_1$–$C_8$ alkoxy, hydroxy, halogen and cyano;
m and n are independently selected are an integer from zero to 10,
$R^1$, $R^2$, $R^3$ and $R^4$ are independently hydrogen or $C_1$–$C_6$ alkyl,
or a pharmaceutically acceptable salt thereof.

14. The method of claim 13, wherein A is an optionally substituted pyridyl, optionally substituted pyrazinyl, optionally substituted quinolinyl or optionally substituted benzothiazolyl.

15. The method of claim 14, wherein said optionally substituted pyridyl is 2-pyridyl, 3-pyridyl or 3-(2,6-dimethylpyridyl).

16. The method of claim 15, wherein n is 1 and B is an optionally substituted phenyl group.

17. The method of claim 16, wherein said optionally substituted phenyl group is phenyl, p-methoxyphenyl or 4-hydroxy-3-methoxy-5-methylphenyl.

18. The method of claim 14, wherein n is an integer from 0 to 6 and B is hydrogen.

19. The method of claim 18, wherein n is 0, 1 or 5.

20. The method of claim 13, wherein $R^1$, $R^2$, $R^3$ and $R^4$ are the same and are methyl, ethyl or isopropyl.

21. The method of claim 13, wherein said modulation of said apoE levels in said patient comprises increasing said apoE levels.

22. The method of claim 21, wherein said compound of claim 1 is selected from the group consisting of:
tetramethyl N-(2-pyridyl)aminomethylenediphosphonate;
tetraethyl N-(2-pyridyl)aminomethylenediphosphonate;
tetraethyl N-(3-pyridyl)aminomethylenediphosphonate;
tetraethyl N-[3-(2,6-dimethylpyridyl)]aminomethylenediphosphonate;
tetraethyl N-(3-quinolinyl)aminomethylenediphosphonate;
tetraethyl N-[2-(2-pyridyl)ethyl]-N-methyl-aminomethylenediphosphonate;
tetraethyl N-(2-pyridyl)-N-(benzyl)-aminomethylenediphosphonate;
tetraethyl N-(2-pyridyl)-N-(p-methoxybenzyl)-aminomethylenediphosphonate;
tetraethyl N-(2-pyridyl)-N-(n-pentyl)-aminomethylenediphosphonate; and
tetraethyl N-(2-pyridyl)-N-(4-hydroxy-3-methoxy-5-methylbenzyl)-aminomethylenediphosphonate.

23. The method of claim 21, wherein said patient is suffering from atherosclerosis, Alzheimer's disease, macular degeneration, retinitis pigmentosa, stroke, degenerative neuropathy, xanthoma or xanthelasma.

24. The method of claim 23, wherein said degenerative neuropathy is associated with diabetic neuropathy or multiple sclerosis.

25. A method of elevating high density cholesterol, comprising administration of a compound of formula (I) according to claim 21.

26. A method for preventing and/or treating atherosclerosis, comprising administration of a compound of formula (1) according to claim 21.

27. A method for preventing and/or treating macular degeneration and retinitis pigmentosa comprising, administration of a compound of formula (1) according to claim 21.

28. A method for the preventing and/or treating stroke, comprising administration of a compound of formula (I) according to claim 21.

29. A method for the prevention of degenerative neuropathy, comprising administration to a compound of formula (I) according to claim 21.

30. The method of claim 29, wherein said degenerative neuropathy is associated with diabetic neuropathy or multiple sclerosis.

31. The method of claim 13, wherein said modulation of said apoE levels in said patient comprises decreasing said apoE levels.

32. The method of claim 31, wherein said compound of formula (I) is selected from the group consisting of:
- tetraisopropyl N-(2-pyridyl)aminomethylenediphosphonate;
- tetraethyl N-(3-pyridylmethyl)aminomethylenediphosphonate;
- tetraethyl N-(2-pyrazinyl)aminomethylenediphosphonate;
- tetraethyl N-(2-benzothiazolyl)aminomethylenediphosphonate;
- tetraethyl N-(2-pyridyl)-N-methyl-aminomethylenediphosphonate; and
- tetraethyl N-(2-pyridylmethyl)aminomethylenediphosphonate.

33. The method of claim 31, wherein said patient expresses apoE4, apoE Leiden or a non-functional mutant form of apoE.

34. The method of claim 31, wherein said patient is suffering from atherosclerosis or Alzheimer's disease.

35. A method for treatment of Alzheimer's disease or dementia comprising administration to a patient an effective amount of a compound of formula (1) as claimed in claim 1.

36. The method of claim 35, wherein said patient is heterozygous or homozygous for apoE2 and/or apoE3 and wherein said compound of formula (I) increases apoE levels in said patient.

37. The method of claim 36, wherein said compound of formula (I) is selected from the group consisting of:
- tetramethyl N-(2-pyridyl)aminomethylenediphosphonate;
- tetraethyl N-(2-pyridyl)aminomethylenediphosphonate;
- tetraethyl N-(3-pyridyl)aminomethylenediphosphonate;
- tetraethyl N-[3-(2,6-dimethylpyridyl)]aminomethylenediphosphonate;
- tetraethyl N-(3-quinolinyl)aminomethylenediphosphonate;
- tetraethyl N-[2-(2-pyridyl)ethyl]-N-methyl-aminomethylenediphosphonate;
- tetraethyl N-(2-pyridyl)-N-(benzyl)-aminomethylenediphosphonate;
- tetraethyl N-(2-pyridyl)-N-(p-methoxybenzyl)-aminomethylenediphosphonate;
- tetraethyl N-(2-pyridyl)-N-(n-pentyl)-aminomethylenediphosphonate; and
- tetraethyl N-(2-pyridyl)-N-(4-hydroxy-3-methoxy-5-methylbenzyl)-aminomethylenediphosphonate.

38. The method of claim 35, wherein said patient is heterozygous or homozygous for apoE4 and said compound of formula (I) decreases apoE levels in said patient.

39. The method of claim 38, wherein said compound of formula (I) is selected from the group consisting of:
- tetraisopropyl N-(2-pyridyl)aminomethylenediphosphonate;
- tetraethyl N-(3-pyridylmethyl)aminomethylenediphosphonate;
- tetraethyl N-(2-pyrazinyl)aminomethylenediphosphonate;
- tetraethyl N-(2-benzothiazolyl)aminomethylenediphosphonate;
- tetraethyl N-(2-pyridyl)-N-methyl-aminomethylenediphosphonate; and
- tetraethyl N-(2-pyridylmethyl)aminomethylenediphosphonate.

* * * * *